US005648535A

United States Patent [19]
Foster et al.

[11] Patent Number: 5,648,535
[45] Date of Patent: Jul. 15, 1997

[54] PROCESS FOR PREPARING ACYL AMINOPHENOLS

[75] Inventors: James A. Foster; Werner H. Mueller; Debra A. Ryan, all of Corpus Christi, Tex.; Hartmut Wiezer, Eppstein/Taunus, Germany

[73] Assignee: Hoechst Celanese Corp., Somerville, N.J.

[21] Appl. No.: 451,338

[22] Filed: May 26, 1995

Related U.S. Application Data

[63] Continuation of Ser. No. 56,555, Apr. 30, 1993, abandoned.
[51] Int. Cl.$^6$ ................................ C07C 231/02
[52] U.S. Cl. ................................ 564/144
[58] Field of Search ................................ 564/144

[56] References Cited

U.S. PATENT DOCUMENTS

| | | | |
|---|---|---|---|
| 3,076,030 | 1/1963 | Freifelder | 260/562 |
| 3,341,587 | 9/1967 | Duesel et al. | 260/562 |
| 3,383,416 | 5/1968 | Benner | 260/575 |
| 3,917,695 | 11/1975 | Schulman et al. | 260/562 A |
| 4,264,525 | 4/1981 | Huber, Jr. | 564/223 |
| 4,670,589 | 6/1987 | Van Ness et al. | 564/144 |

FOREIGN PATENT DOCUMENTS 0 569 792 A2   11/1993   European Pat. Off. .

OTHER PUBLICATIONS

Method der Organischen Chemie (Houben–Weyl) vol. XI/1, 1957, George Thieme Verlag, Stuttgart, pp. 369–382.
Ullmann's Encyclopedia of Industrial Chemistry, vol. 84, 1992, "Stirred–Tank and Loop Reactors", Weinhe.
Ullmann's Encyclopedia of Industrial Chemistry, vol. A13, 1989, "Hydrogenation and Dehydrogenation".
CA(77): 126261u (1972) —Koengetal –"Catalytic Manufacture of p–acetamidophenol"—DE 1493727.
Derwent Abstract —Acc. #C66–F38223—"Production of Para–Acetamido–Phenol From Para–Nitrophenol"—DE 1493727.

*Primary Examiner*—José G. Dees
*Assistant Examiner*—Mary C. Cebulak
*Attorney, Agent, or Firm*—James L. McGinnis

[57] ABSTRACT

A process for the production of N-acylaminophenols by the concurrent hydrogenation of a nitrophenol to an aminophenol and the acylation of the aminophenol with acyl anhydride takes place on a continuous basis in a stirred tank reactor in which liquid product is continuously withdrawn from the reactor. Of particular interest is the manufacture of acetaminophen, N-acetyl-p-aminophenol by continuous reaction of p-ntirophenol, hydrogen and acetic anhydride.

31 Claims, No Drawings

PROCESS FOR PREPARING ACYL AMINOPHENOLS

This is a continuation of application Ser. No. 08/056,555 filed on Apr. 30, 1993, now abandoned.

FIELD OF THE INVENTION

This invention relates to the production of N-acyl-aminophenols by hydrogenation of nitrophenols to aminophenols, and concurrently acylating the aminophenol. The invention has particular use in forming N-acetyl-p-aminophenol by hydrogenation of p-nitrophenol and concurrent acetylation of the formed p-aminophenol as above described in one step and on a continuous basis.

The conventional process for the production of N-acetyl-p-aminophenol involves reduction of p-nitrophenol to produce p-aminophenol which is then acetylated to produce N-acetyl-p-aminophenol. The reduction of p-nitrophenol to produce p-aminophenol involves hydrogenating the p-nitrophenol in the presence of catalysts such as platinum, palladium, nickel, noble metal catalysts, or oxides of platinum, palladium, or noble metal catalysts. Gaseous hydrogen is commonly used as a reducing agent. The acetylating agent is usually acetic anhydride. The reaction medium can be acetic acid, water, a water-isopropanol mixture, or other inert medium.

The above described series of reactions has been carried out simultaneously as in U.S. Pat. No. 3,076,030 and U.S. Pat. No. 3,341,587. In the process described in both of these simultaneous reaction patents, p-nitrophenol and acetic anhydride are added at the beginning of the reaction sequence, and the hydrogenation of the p-nitrophenol takes place in the presence of acetic anhydride that is in excess over the amount of p-aminophenol in the system at any given moment. The one-step synthesis of APAP is advantageous in that such process avoids the need to isolate and purify the p-aminophenol which is oxidatively unstable.

The above reaction sequence has also been carried on a step-wise manner in which the hydrogenation of p-nitrophenol is completed prior to the acetylation step. This step-wise reaction scheme has been further refined in U.S. Pat. No. 4,264,525 in which the hydrogenation step is interrupted and acetylation accomplished followed by at least one further hydrogenation step each of which is followed by another acetylation step all the while keeping the pH below about 7.0. In U.S. Pat. No. 4,670,589, at least 5% of p-nitrophenol is first hydrogenated to p-aminophenol, and then the remaining nitrophenol is hydrogenated while concurrently acetylating p-aminophenol to N-acetyl-p-aminophenol wherein, prior to hydrogenating 80% of the p-nitrophenol, no molar excess of acetic anhydride is provided.

The step-wise reaction schemes described above are cumbersome and are particularly difficult to operate on a commercial scale, as such schemes require delicate control to ensure that the correct percentage of the initial reduction reaction has taken place before initiation of the acetylation reaction. Even the single step reactions have not been overly efficient as such processes are typically run in batch reactors. Unfortunately, it has been found that nitro reductions, especially of aromatic compounds involve the sequential reduction of highly reactive and unstable intermediates, including nitroso-, hydrazo-, azo-, and azoxy-compounds. These reactive intermediates can lead to several undesirable by-products, which are often very highly colored. The batch reductions cannot minimize these reactive intermediates.

Similarly, the conversion of the para-nitrophenol to the acetyl-derivative thereof is highly exothermic. In the batch process, the heat release from the reaction continually changes rendering it difficult to provide accurate temperature control.

It has been suggested in U.S. Pat. No. 3,076,030 that the single step scheme for concurrently reacting para-nitrophenol and acetic anhydride to N-acetyl-p-aminophenol can easily be adapted to a continuous process in which hydrogen, nitrophenol, inert solvent, if used, and acetic anhydride are conducted concurrently or countercurrently over a bed of palladium catalyst. However, because the conversion of the para-nitrophenol to the acetylated derivative is highly exothermic, the diameter of any fixed bed reactor will be limited by the amount of cooling which can be applied externally and, accordingly, the concentration of para-nitrophenol in the feed will have to be limited by the rate of heat removal.

It has been known to reduce aromatic nitro compounds on a continuous basis in a stirred tank reactor. However, the use of a stirred tank reactor to conduct a one-step process in which an aminophenol and the acylated derivative thereof are formed concurrently on a continuous basis has not been previously suggested in the prior art.

Because of its use as an analgesic, N-acetyl-p-aminophenol must be very pure and must not be colored. The process of this invention produces N-acetyl-p-aminophenol that is less colored than that produced by prior art batch processes. In fact, it has been shown that N-acetyl-p-aminophenol can be manufactured in accordance with the present invention as below-described as a pure white solid crystalline product. Additionally, this invention produces N-acetyl-p-aminophenol continuously in a shorter time than prior art processes since it obviates the multiple equipment clean-ups and turn-arounds. Still further, this process does not require complex temperature control as in batch reactions or continuous bed reactors.

SUMMARY OF THE INVENTION

This invention provides a process for producing N-acylaminophenols comprising, catalytically hydrogenating a nitrophenol to an aminophenol and concurrently acylating the aminophenol to an N-acylaminophenol with an acyl acid anhydride on a continuous basis in a stirred tank reactor. Compared to batch hydrogenation, the continuous process affords a high purity product by minimizing the concentration of reaction intermediates which form highly colored by-products. The continuous process is also simpler to operate. Heat release is constant and easily controlled compared to batch reactions where the heat release continually changes.

DETAILED DESCRIPTION OF THE INVENTION

According to the present invention, a nitrophenol is reduced with gaseous hydrogen in the presence of a hydrogenation catalyst and at least one equivalent of an acyl anhydride to produce an N-acylaminophenol. Surprisingly, the reduction of the nitrophenol can be carried out at room temperature and at relatively low pressures compared with the reactions described in the prior art, but higher pressures and/or temperatures may of course be used. Importantly, the reaction takes place on a continuous basis in a stirred tank reactor from which product is continuously removed. The process produces a yield of at least 75%, typically a yield of at least 98% of acylaminophenol of excellent quality, purity, color, and appearance.

The nitrophenols useful as reagents in this invention include p- and o-nitrophenol and derivatives thereof in which one or more aromatic ring hydrogens are replaced with substituents which do not adversely affect the desired concurrent reactions. The term acyl acid anhydride is used to describe acylating agents having the formula

wherein $R^1$ is a member of the group consisting of $C_1$–$C_4$ alkyl and $R^2$ is H, or $C_1$–$C_3$ alkyl although there is no known reason to expect that the higher alkyl compounds will not behave in like manner given the proper reaction conditions.

In the most preferred embodiment of the invention N-acetyl-p-aminophenol is produced by concurrently hydrogenating p-nitrophenol (PNP) and acetylating the p-aminophenol with acetic anhydride.

The process of the present invention can be carried out at room temperature, but higher temperatures between about 50° and 175° C. are preferred. Preferably, temperatures between about 60°–100° C. are used. The process may be carried out at a hydrogen pressure between 1 atmosphere to 100 atmospheres. Preferably, pressures of from about 5 atm to 50 atm are used. The amount of catalyst, calculated as actual metal in units of the starting material nitrophenol, is between 0.05 and 30 wt. %. Excellent results are obtained by using finely divided palladium metal, palladium on charcoal, platinum, silica gel, alumina, kieselguhr, chromium oxide, zirconium oxide, bentonite, asbestos, etc. Palladium on carbon is preferred. The catalyst itself may be in the form of pellets, granules, powder, etc. and the metal may be precipitated on the carrier in the form of the metal or compound thereof which is reduced in situ in the presence of hydrogen.

The reactions of the present invention may be carried out in an inert solvent, although no advantage is seen in increasing the volume of the reaction mixture above that required to keep the reaction mixture in solution at the temperature of the reaction. Solvents such as ethers or hydrocarbons and organic acids may be used. The term "inert" is meant to express that the diluent does not react with the starting material, the end product of the reaction, the intermediary aminophenol, the catalyst, or the acyl anhydride used in the reaction. Most conveniently, the acid related to the anhydride is used as a diluent since it does not add any undesirable ingredients to the reaction mixture. Alternatively, the solvent may be a compound which will react with any small molecule which could be a by-product of the reaction, i.e., alcohols, e.g., butanol to react with the acid remaining after acylating the amine with the acyl anhydride.

The amount of acyl anhydride to take part in the reaction is chosen between one equivalent and any reasonable excess thereover. Excellent results are obtained by using 1 to 1.2 equivalents of anhydride per equivalent of nitrophenol. Large excesses of anhydride are to be avoided since they may lead to the diacylated product.

The reactor which is utilized in the process of the present invention is a stirred tank reactor which is self descriptive and simply comprises a tank which is fitted with one or more impellers to ensure optimal mixing. The tank can be baffled to further enhance mixing of the reactants. In operation, the nitrophenol, acyl anhydride and inert solvent such as the acid related to the anhydride reactant and catalyst are fed to the reactor. Hydrogen is bubbled in to reduce the nitrophenol to the aminophenol. Catalyst slurry concentrations such as palladium on carbon typically range from about 1 to 30 wt. % of the reactor contents. The nitrophenol will typically comprise between about 10 and 40 wt. % of the reactor feed. Higher amounts of the nitrophenol reduce the amount of the solvent needed in the reactor and the amount which must be recycled. Residence time in the reactor will vary depending upon temperature, the amount of catalyst present as well as the amount of hydrogen pressure and excess of acyl anhydride present but generally will range from about 0.25 to 2 hours with less than 1 hour being typical. Product is continuously drawn from the reactor. The percentage of product in the reactor will vary depending upon the concentration of the nitrophenol fed to the reactor but it is preferred to maintain the level of product at from about 25 to 40 wt. %. Catalyst which is removed from the reactor can be recycled. For example, the palladium on carbon catalyst is reusable. The catalyst concentration in the reactor should remain constant. The catalyst can be maintained in the reactor by various means including use of filters in the product liquid stream and, alternatively, by forming a quiescent zone in the reactor by the action of the stirrer, use of baffles or by a similar means in which the product is drawn off from the reactor from within the quiescent zone to minimize withdrawing catalyst.

The following examples are only intended to illustrate this invention and are not intended in any way to limit the scope of the invention. All parts and percentages are by weight unless otherwise noted.

EXAMPLES 1–12

Manufacture of N-acetyl-p-aminophenol (APAP)

A 2L continuous stirred tank reactor (CSTR) was used for the examples. The reactor consisted of a 2L stirred autoclave, manufactured by Autoclave Engineers Co., and configured to have a 1400 mL working volume. The autoclave was baffled and fitted with two impellers to optimize mixing. The entire unit was constructed of 316 stainless steel and could be operated at a maximum pressure of 800 psig and maximum temperature of 138° C. An internal filter was installed on the product take-off line to keep the catalyst in the reactor.

The catalyst used was a 3% Pd on carbon catalyst (50% water-wet) manufactured by Precious Metals Corp. The hydrogenation catalyst, 28 g, was charged to the empty reactor. This charge represented a 2 wt. % loading. Glacial acetic acid was pumped into the reactor until it reached an appropriate level.

Para-nitrophenol (PNP), purchased from Aldrich Chemical Co. (98% nominal purity) was dissolved in glacial acetic acid (Baker Analyzed) in a 2.5 gal. container, purged of air with a nitrogen sweep and connected to the intake of one of the reactor's positive displacement pumps. A sample of the PNP feed solution was analyzed by gas-phase chromatography. Acetic anhydride, purchased from Aldrich (99+%), was used either as received or in some runs diluted with glacial acetic acid to accommodate the pump rates attainable with the unit's second positive displacement pump. Nitrogen was used to sweep air from the acetic anhydride also. The PNP feed solution and the acetic anhydride feed were pumped continuously to the reactor using scales to obtain weight data. The feed pump rates were adjusted to maintain a slight mole excess of acetic anhydride.

Hydrogen was fed to the reactor as it was consumed by reaction, while maintaining a constant hydrogen pressure.

The APAP product stream at reaction temperature was continuously collected in a 2.5 gal. container under a constant purge of nitrogen. About 1500–1600 g of the product stream at the end of the run were collected for isolation of the APAP.

A portion of the product stream was transferred to a rotary evaporator, minimizing air exposure. Acetic acid and water (of reaction) were removed overhead using vacuum (20 in. Hg) and minimal heating (~70° C.) until a semi-solid mass formed. The semi-solid mass was filtered using a sintered glass Buchner funnel and cold (~5° C.) deionized water was used to wash the APAP cake. A 1.8 to 1 w/w water to APAP wash ratio was used and divided into two or three portions. The mother liquor and wash solutions were typically combined and analyzed by GC. The wet APAP cake was dried in a vacuum oven at 45° C. overnight under house vacuum with a slight nitrogen purge. Reaction conditions, feed rates and reactivity data are set forth in Table I. APAP product purity is described in Table II.

Regarding the conversion of PNP with respect to reactor pressure, it was found that at 100° C., a large decrease in reaction pressure from 500 psig to 150 psig decreased the PNP conversion, from 100% to 92% at comparable STY.

STY was calculated as mols APAP per liter of reactor liquid volume per hour. The STY was varied by varying the PNP and Ac2O feed rates. At the highest rates studied, 3–4 mol/L/h, the conversion of PNP was not significantly affected.

The purity of the vacuum oven-dried crude APAP samples was determined by GC. Purities were typically 99–99.5 wt. % APAP, with minor traces of 4-acetoxyacetaminophen, and occasional unknown heavier than APAP, acetic acid and water. The analyses are summarized in Table II. When the

TABLE I

| Run No. | Feed g/min PNP soltn. | Ac2O | Wt. % PNP Entering Reactor | RT, min | T °C. | P psig | Mole Ratio Ac2O/ PNP | STY, mols APAP/ L/h | % SEL, norm | % PNP CONV |
|---|---|---|---|---|---|---|---|---|---|---|
| 1 | 30 100 wt. % | 3 Ac2O | 10 | 42 | 60 | 500 | 1.3 | 1.0 | 95.6 | 98.9 |
| 2 | 34.7 100 wt. % | 5.82 Ac2O | 19 | 35 | 60 | 500 | 1.0 | 2.4 | 98.2 | 99.8 |
| 3 | 32.8 100 wt. % | 5.4 Ac2O | 19 | 37 | 60 | 500 | 0.99 | 2.3 | 98.3 | 99.5 |
| 4 | 30.4 50 wt. % | 15.3 Ac2O | 23 | 31 | 60 | 500 | 0.98 | 3.3 | 98.5 | 99.4 |
| 5 | 30.0 50 wt. % | 14.3 Ac2O | 24 | 32 | 100 | 500 | 0.90 | 3.3 | 99.4 | 100.0 |
| 6 | 29.7 50 wt. % | 15.5 Ac2O | 18 | 31 | 100 | 500 | 1.3 | 2.5 | 98.1 | 99.7 |
| 7 | 43.4 50 wt. % | 23.1 Ac2O | 19 | 21 | 100 | 500 | 1.3 | 3.8 | 98.3 | 99.2 |
| 8 | 44.8 50 wt. % | 22.7 Ac2O | 18 | 21 | 138 | 500 | 1.2 | 3.8 | 98.0 | 99.6 |
| 9 | 30.9 50 wt. % | 15 Ac2O feed | 19 | 31 | 100 | 250 | 1.2 | 2.7 | 98.1 | 97.2 |
| 10 | 39.7 100 wt. % | 10.6 Ac2O feed | 22 | 28 | 100 | 150 | 1.3 | 3.4 | 97.2 | 91.6 |
| 11 | 30.4 50 wt. % | 14.7 Ac2O feed | 21 | 31 | 100 | 500 | 1.1 | 2.9 | 99.4 | 100.0 |
| 12 | Batch Run | | Recycled ML + 1st wash from Run No. 10 33 | *na | 100 | 350–600 | 1.2 | na | 99.1 | na |

*na = not applicable.

TABLE II

| Sample No. | Wt. % PNP | Wt. % PAP | Wt. % APAP | Wt. % AAA[1] | Wt. % Unks | Wt. % HOAc | Wt. % H$_2$O |
|---|---|---|---|---|---|---|---|
| 1 | 0.49 | 0.0 | 98.0 | 1.00 | — | 0.0 | 0.54 |
| 2 | 0.0 | 0 | 97.9 | 0.3 | — | 0.0 | 0 |
| 3 | 1.7 | 0.14 | 96.6 | 1.09 | 0.00 | 0.0 | 0.46 |
| 4 | 0.42 | 0.0 | 96.5 | 0.94 | 0.00 | 2.1 | 0 |
| 5 | 0.0 | 0.0 | 99.8 | 0.08 | 0.00 | 0.15 | 0 |
| 6 | 0.0 | 0.2 | 99.6 | 0.15 | 0.10 | 0.1 | 0.09 |
| 7 | 0.00 | 0.03 | 99.6 | 0.14 | 0.04 | 0.1 | 0.09 |
| 8 | 0.00 | 0.03 | 99.5 | 0.28 | 0.02 | 0.20 | 0.07 |
| 9 | 0.0 | 0.0 | 99.5 | 0.11 | 0.09 | 0.2 | 0.14 |
| 10 | 0.0 | 0.0 | 98.9 | 0.15 | 0.17 | 0.3 | 0.37 |
| 11 | 0.0 | 0.0 | 99.5 | 0.10 | 0.07 | 0.15 | 0.12 |
| 12 (Batch) | 0.0 | 0.0 | 99.2 | 0.12 | 0.24 | 0.4 | 0.12 |

[1]4-acetoxyacetaminophen

There appeared to be little effect on the conversion of PNP relative to reaction temperature. However, a more sensitive measure of the extent of PNP conversion showed that there was a slight increase in the level of PNP in the final product at 60° C. compared to 100° or 138° C. Additionally, there was a slightly higher impurity level in the crude (dried) APAP synthesized at the lower temperature, 60° C. The impurity level decreased at the higher temperatures.

analyses are normalized to a water-free, acetic acid-free product, the normalized APAP purities are typically 99.6–99.8 wt. %. In Run 11, the mother liquor and the first wash liquor from the prior run 10 were recycled to the PNP feed solution. This amounted to an addition of 26 g APAP to the PNP feed, 11 g PNP, about 5 g of unknowns and 200 g water primarily from the wash liquor. The limit of color "LOC" of the product obtained from the run was still very low indicating the recycle of the unknowns did not adversely affect the crude product quality. The presence of water in the feed did not decrease the PNP solubility as a 31 wt. % PNP feed was still soluble at room temperature.

The batch Run 12 was carried out in the same reactor to compare with the CSTR operability and product purity. From the results in Table I and II, the batch run gave a surprisingly pure product based on GC analysis. The batch APAP, however, was light yellow in color, not nearly as white as the CSTR product. Although not specifically measured, it is believed that the LOC of the batched material would have been significantly higher than the APAP resulting from the CSTR runs. Operation of the batch run in the lab was much more difficult than the continuous run resulting in loss of control of the reaction temperature.

EXAMPLES 13–20

The 2L CSTR, used in Examples 1–12 was modified slightly. To attempt a higher solids loading in the reactor, the unit feed lines and product take-off lines were heat-traced with electrical heating tapes. The pump head for the PNP feed was also heated by placing a large heating mantle over the head.

remained in solution at the process temperature. The crude APAP product stream exited the reactor continuously as a hot solution. Hydrogenation catalyst remained in the reactor by means of a filter installed on the product take-off line inside the reactor and submersed in the liquid phase as in the previous examples. Crude APAP was isolated from the product stream after flashing about 50% by weight of the solvent (acetic acid and water) overhead in a rotary evaporator. The remaining slurry of APAP was crash crystallized at ~15 C and filtered from which the mother liquor (ML) was obtained. The crude APAP cake was washed with an equal weight of cold water, twice filtering off the wash liquors after every wash. The crude wet APAP cake was dried in the vacuum oven at 45°–50° C. and 20" Hg to give a dried crude APAP cake.

Tables III–IV summarize the process conditions, feed rates and product analyses of all the runs. The two batch runs 19 and 20 caused irreversible deterioration of the hydrogenation catalyst.

TABLE III

| Run No. | Feed g/min. PNP soltn. | Ac20 | Wt. % Entering Reactor PNP | APAP | Rt, min | T °C. | P psig | Mole Ratio Ac2O/ PNP | STY, mols Feed/ L/h | % SEL, norm | % PNP CONV |
|---|---|---|---|---|---|---|---|---|---|---|---|
| 13 | 29 No recycle | 8 | 31.7 | 0.0 | 38 | 100 | 500 | 0.9 | 3.6 | 97.4 | 99.9 |
| 14 | 26 Recycled ML from 13 | 9 | 28.9 | 0.0 | 41 | 100 | 500 | 1.2 | 3.1 | 98.2 | 99.3 |
| 15 | 28 Recycled ML from 14 | 8 | 30.0 | 0.6 | 39 | 100 | 500 | 1.1 | 3.4 | 98.3 | 98.8 |
| 16 | 25 Recycled ML from 15 | 8 | 30.8 | 0.2 | 42 | 100 | 500 | 1.1 | 3.2 | 98.2 | 100 |
| 17 | 24 Recycled ML from 16 | 8 | 29.7 | 0.0 | 43 | 100 | 500 | 1.2 | 3.0 | na | na |
| 18 | 25 Recycled ML from 17 and added solid APAP | 8 | 28.3 | 3.0 | 42 | 100 | 500 | 1.2 | 3.2 | 97.5 | 100 |
| 19 | Batch run (operational difficulties delayed addition of AC20) | — | | | | ~100 | ~500 | — | — | 96.7 | 95.8 |
| 20 | Batch run (reaction time) | | | | 60 | 72–104 | 200–500 | — | — | 99.0 | 90.0* |

*M.L. highly colored

TABLE IV

| | APAP Product Purity | | | | | | | |
|---|---|---|---|---|---|---|---|---|
| Sample No. | Wt. % PNP | Wt. % PAP | Wt. % APAP | Wt. % AAA | Wt. % IMP | Wt. % HOAc | Wt. % H$_2$O | LOC |
| 13 | 0.00 | 0.00 | 99.20 | 0.15 | 0.00 | 0.7 | 0.12 | 0.012 |
| 14 | 0.00 | 0.00 | 99.39 | 0.21 | 0.00 | 0.3 | 0.11 | 0.016 |
| 15 | 0.00 | 0.00 | 99.22 | 0.11 | 0.00 | 0.6 | 0.1 | 0.020 |
| 16 | 0.00 | 0.00 | 98.77 | 0.12 | 0.00 | 0.6 | 0.08 | 0.033 |
| 17 | 0.00 | 0.00 | 99.10 | 0.14 | 0.00 | <0.6 | 0.16 | 0.028 |
| 18 | 0.00 | 0.00 | 99.30 | 0.00 | 0.00 | 0.6 | 0.08 | 0.038 |
| Batch Runs | | | | | | | | |
| 19 | 0.00 | 0.00 | 98.95 | 0.51 | 0.00 | 0.5 | 0.1 | 0.087 |
| 20 | 0.00 | 0.00 | 99.19 | 0.00 | 0.00 | 0.7 | 0.1 | 0.182 |

PNP, dissolved in glacial acetic acid, and acetic anhydride were fed concurrently and continuously to the 2L autoclave in which PNP was catalytically hydrogenated to PAP and subsequently acetylated by the anhydride to APAP which The LOC values for the dry APAP cake were analyzed by a control chart. The upper control limit was 0.055 and the lower control limit was 0.018. From Table IV, it can be seen that APAP product from the CSTR had useful LOC values and had substantially improved color relative to the batch runs.

The average selectivity (normalized for PNP conversion to APAP for the CSTR runs was 98.3 0.8%. One of the inefficiencies was due to AAA. Unidentified impurities included two light ends eluting before PAP, five impurities eluting after PNP, but before APAP, and four heavy ends, eluting after AAA.

The average conversion of PNP in the CSTR runs was 99.4 0.8% at an average STY (space time yield) of 3.4 0.4 mols APAP per L of reactor liquid volume per hour.

In the batch runs 19 and 20, about 30% of the PNP charge was hydrogenated before the addition of the acetic anhydride charge. The composition of the batch reactor was analyzed immediately before the addition of the anhydride. A 28% PNP conversion to PAP occurred in Run 19 and a 22% PNP conversion to PAP occurred in Run 20 before the addition of the anhydride. Exact temperature control at the desired reaction temperature of 100 C was not possible initially because of the very large exotherm occurring at the initiation of the batch runs. In the CSTR mode, temperature control was never a problem and varied no more than 1 to 2 degrees.

The batch runs gave selectivities of 96.7% and 99.0% which are similar to the CSTR selectivities. However, both batch runs had LOC's which were higher than the upper control limit set by the preceding CSTR runs. The mother liquors from both the batch runs were high in PNP and PAP resulting from a difficulty in achieving 100% conversion in the batch operation.

The conversions obtained for the batch runs were significantly lower, 95.8% for one run and 90.0% for the other, than for the CSTR runs. It was more difficult to obtain complete conversion in the batch runs which left higher levels of PNP and PAP, both potential color-precursors.

The Pd/C catalyst appeared to lose activity during these batch runs which probably accounted for the incomplete conversion of PNP and PAP. Hydrogenation intermediates of PNP which are not minimized in the batch operation may result in higher molecular weight by-products that poison the catalyst surface. CSTR operation generally improved catalyst life compared to batch.

The STY was estimated for the second batch Run 20 to be about 1.4 mols APAP/L/h. This was significantly less than the 3.4 0.4 mols APAP/L/h measured for the CSTR runs.

EXAMPLES 21–24

A few runs in a trickle bed reactor were done to compare APAP quality and reactor productivity to the CSTR. A trickle bed was expected to give a lower product quality similar to a batch hydrogenation. However, capital can be lower for a trickle bed than a stirred reactor.

A simple trickle bed reactor was constructed from 2" diameter pipe with a 20" catalyst bed length. The pressure rating of the reactor was 150 psig. Heating was supplied by heating tapes wrapped on the outside of the reactor tube. The reactor held 1L of catalyst. An Engelhard 0.5% Pd/C catalyst of 4×8 mesh was chosen for study.

A total of four trickle bed runs were done. The reaction was so exothermic that temperature control could only be accomplished by decreasing the concentration of PNP in the feed. Because of this, comparable concentrations to that used in the CSTR work could not be run in the trickle bed while maintaining a reaction temperature which was comparable to CSTR work.

In the first experiment, with a 16 wt. % PNP concentration entering the reactor (after dilution with acetic anhydride), the reaction temperature lined out at 200° C. with no external heating applied. To obtain reactor temperatures of ~100° C., the PNP concentration entering the reactor was decreased to 3–4 wt. %. Three runs were done at these PNP concentrations which resulted in a temperature of 110° C. when steady-state was achieved. Process conditions, feed rates and results are shown in Tables V and VI.

Reaction selectivities were dependent upon the temperature and PNP feed rate. At 200° C., the selectivity of PNP to APAP was only 87% at 70% conversion, and increased to 94–97% at 110° C. at a lower feed rate, and complete conversion obtained at 110° C. only, and only 70% at 200° C. because of the higher PNP concentration in the feed.

The selectivities obtained with the trickle bed were poorer than that obtained with the CSTR, at similar, but not identical reaction conditions. Comparison at the same conversion, preferably 100%, is probably most indicative of real differences.

When trickle bed and CSTR selectivities were compared, the data showed that the selectivity was improved by ~3% absolute in the CSTR. Additionally, some highly colored species were present in the mother liquor and wash liquors in the last two trickle bed runs. Green to dark blue liquors resulted. Analysis by X-ray indicated the colored species were probably organic in nature, since trace metals which could result from corrosion of stainless steel were not detected. APAP color is an extremely important parameter in final product quality and presence of color in the liquors indicated that the same species may be a contaminant in the APAP also. Also, the feasibility of recycling these liquors is highly questionable.

The LOC's obtained for the final crude (dry) APAP varied greatly over the four runs. The LOC for the product obtained at 200° C. was very poor, 1.295, probably a direct result of the high reaction temperature. At 110° C., the LOC's were much lower, but varied with the run. In run 22, the relatively high LOC of 0.234 was probably due to the manner in which this sample was washed. A fresh water wash was not used to rinse the crude cake after removal of the mother liquor, as for runs 23 and 24 which had low LOC's of 0.023 and 0.055. These latter numbers are comparable to LOC's obtained with the CSTR.

Because the conversion of PNP to APAP is highly exothermic, the diameter of a trickle bed reactor tube will be limited by the amount of cooling which can be applied externally and the PNP concentration in the feed will be limited by this rate of heat removal. A CSTR has relatively more surface area available for cooling and additionally there is no peak heat release in a CSTR compared to a trickle bed. Inherently, then, a CSTR will be able to out-produce a trickle bed.

Because no external cooling was built into the simple lab trickle bed, the STY achieved in this reactor was lower than probably could be achieved. Still, the STY obtained in the trickle bed was an order of magnitude less than that achieved in the CSTR. As reported in Table V, at 100% PNP conversion, the STY achieved with the trickle bed was only 0.2–0.3 mols APAP per liter of catalyst volume per hour. With the CSTR, a maximum STY of 4 mols APAP per liter per hour was achieved.

TABLE V

Trickle Bed

| Run No. | Pump Rate g/min PNP | Pump Rate g/min Ac2O | Wt. % PNP Entering Reactor | RT, min | T °C. | P psig | Mole Ratio Ac2O/ PNP | STY, mols APAP/ L/h | % SEL, norm | % PNP CONV |
|---|---|---|---|---|---|---|---|---|---|---|
| 21 | 21.4 of 20% PNP soln | 4.9 | 16.3 | 3 | 200 | 100 | 0.8 | 1.8 | 87.4 | 70.0 |
| 22 | 13.6 of 5% PNP soln | 5.2 | 3.6 | 4 | 110 | 100 | 1.3 | 0.3 | 96.7 | 100 |
| 23 | 7.5 of 5% PNP soln | 5.2 | 3.0 | 6 | 110 | 100 | 2.4 | 0.2 | 95.3 | 100 |
| 24 | 10.1 of 5% PNP soln | 4.8 | 3.4 | 5 | 110 | 100 | 1.6 | 0.2 | 94.3 | 100 |

TABLE VI

APAP Product Purity

| Sample No. | Wt. % PNP | Wt. % PAP | Wt. % APAP | Wt. % AAA | Wt. % IMPs | Wt. % HOAc | Wt. % H2O | LOC |
|---|---|---|---|---|---|---|---|---|
| 21 | 0.84 | 0.00 | 98.08 | 1.27 | 0.00 | 0.00 | 0.34 | 1.295 |
| 22 | 0.00 | 0.00 | 98.70 | 0.76 | 0.00 | ~0.4 | 0.18 | 0.234 |
| 23 | 0.00 | 0.00 | 97.10 | 0.90 | — | 1.70 | 0.34 | 0.023 |
| 24 | 0.00 | 0.00 | 96.90 | 1.30 | 0.00 | 1.60 | 0.20 | 0.055 |

EXAMPLE 25

In this example, Run No. 8 is repeated except that instead of para-nitrophenol as the feed, o-nitrophenol is utilized to produce N-acetyl-o-aminophenol. The process conditions for Run No. 8 are set forth in Table 1. Conversion of the nitrophenol is greater than 99% and the selectivity to N-acetyl-o-aminophenol is greater than 98%.

EXAMPLE 26

Run No. 8 is again repeated in the 2L stirred tank reactor as previously described except that instead of acetic anhydride, butyric anhydride is utilized and, instead of the acetic acid solvent, butyric acid is used. The feed rate for the butyric anhydride to the CSTR is 35.2 grams per minute and is diluted to 50 wt. % in butyric acid. All operating conditions are again equivalent to that stated in Table 1. What is formed is N-butyryl-p-aminophenol. Conversion of the para-nitrophenol is approximately 99% and the selectivity to the product is greater than 98%.

What is claimed is:

1. A process for producing N-acylaminophenols comprising simultaneously and continuously adding a nitrophenol, an acyl anhydride, and hydrogen to a continuous stirred tank reactor, wherein said acyl anhydride is added at a rate of at least about one equivalent per equivalent of said nitrophenol; hydrogenating said nitrophenol to an aminophenol in the presence of a slurry of a hydrogenation catalyst and concurrently acylating said aminophenol with said acyl anhydride in said reactor to form an N-acylaminophenol product; and continuously withdrawing said product from said reactor.

2. The process of claim 1 wherein said acyl anhydride is added at a molar rate ranging from about an equal amount to a 20% excess relative to said nitrophenol.

3. The process of claim 1 wherein said continuous stirred tank reactor is maintained at a temperature of from about 50° to 175° C.

4. The process of claim 3 wherein said continuous stirred tank reactor is maintained at a temperature of from between about 60° to 100° C.

5. The process of claim 1 wherein said nitrophenol is hydrogenated under a hydrogen pressure of from about 1 atmosphere to 100 atmospheres.

6. The process of claim 5 wherein said nitrophenol is hydrogenated under a hydrogen pressure of from about 5 atm to 50 atm.

7. The process of claim 1 wherein said hydrogenation catalyst is palladium.

8. The process of claim 7 wherein said hydrogenation catalyst is palladium supported on carbon.

9. The process of claim 1 wherein said nitrophenol is fed to said reactor dissolved in a solvent.

10. The process of claim 1 wherein said product is withdrawn from said reactor in the form of a liquid.

11. The process of claim 1 wherein the residence time of reactants in the reactor ranges from about 0.25 to 2 hours.

12. The process of claim 10 wherein a solid product is crystallized from said liquid product leaving said reactor and the liquid which remains from said crystallization is recycled to said reactor.

13. The process of claim 1 wherein said acyl anhydride has a structural formula of $(R^1CO)_2O$ or $R^2HC=C=O$, wherein $R^1$ is a $C_1-C_4$ alkyl and $R^2$ is H, or $C_1-C_3$ alkyl.

14. The process of claim 1 wherein said nitrophenol is selected from the group consisting of p- and o-nitrophenol and substituted derivatives thereof.

15. The process of claim 15 wherein said nitrophenol is p-nitrophenol and said acyl anhydride is acetic anhydride.

16. The process of claim 15 wherein said acetic anhydride is added at a molar rate ranging from about an equal amount to a 20% excess relative to said p-nitrophenol.

17. The process of claim 15 wherein said continuous stirred tank reactor is maintained at a temperature of from about 50° to 175° C.

18. The process of claim 15 wherein said p-nitrophenol is hydrogenated under a hydrogen pressure of from about 1 atmosphere to 100 atmospheres.

19. The process of claim 18 wherein said p-nitrophenol is hydrogenated under a hydrogen pressure of from about 5 atm to 50 atm.

20. The process of claim 15 wherein said hydrogenation catalyst is palladium.

21. The process of claim 15 wherein said hydrogenation catalyst is platinum.

22. The process of claim 15 wherein said hydrogenation catalyst is palladium supported on carbon.

23. The process of claim 15 wherein said p-nitrophenol is fed to said reactor dissolved in a solvent.

24. The process of claim 23 wherein said solvent is acetic acid.

25. The process of claim 15 wherein said product is withdrawn from said reactor in the form of a liquid.

26. The process of claim 15 wherein the residence time of reactants in the reactor ranges from about 0.5 to 2 hours.

27. The process of claim 15 wherein a solid product is crystallized from said liquid product leaving said reactor and the liquid which remains from said crystallization is recycled to said reactor.

28. The process of claim 1, wherein the conversion of said nitrophenol is at least about 92%.

29. The process of claim 1, wherein the conversion of said nitrophenol is at least about 97%.

30. The process of claim 1, wherein said catalyst may be in the form of pellets, granules, or powder.

31. The process of claim 1, wherein the amount of said acyl anhydride is in the range of about 1 to about 1.2 equivalents per equivalent of said nitrophenol.

* * * * *